US007078413B2

(12) United States Patent
Kudsk

(10) Patent No.: US 7,078,413 B2
(45) Date of Patent: *Jul. 18, 2006

(54) COMPOSITIONS AND METHODS OF USE FOR A BOMBESIN PEPTIDE

(75) Inventor: Kenneth A. Kudsk, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 509 days.

This patent is subject to a terminal disclaimer.

(21) Appl. No.: 10/152,611

(22) Filed: May 21, 2002

(65) Prior Publication Data

US 2003/0166539 A1    Sep. 4, 2003

Related U.S. Application Data

(63) Continuation-in-part of application No. 09/730,801, filed on Dec. 7, 2000, now Pat. No. 6,576,611, which is a continuation-in-part of application No. 08/842,877, filed on Apr. 17, 1997, now abandoned.

(60) Provisional application No. 60/029,689, filed on Oct. 31, 1996, provisional application No. 60/015,835, filed on Apr. 19, 1996.

(51) Int. Cl.
*A61K 38/26* (2006.01)
*C07K 7/00* (2006.01)

(52) U.S. Cl. ...................................... 514/308; 530/300
(58) Field of Classification Search ................ 530/308
See application file for complete search history.

(56) References Cited

U.S. PATENT DOCUMENTS

| 5,354,747 | A | * | 10/1994 | Hansen et al. | ......... | 514/211.14 |
|---|---|---|---|---|---|---|
| 5,428,018 | A | | 6/1995 | Edwards et al. | ............... | 514/15 |
| 5,428,019 | A | | 6/1995 | Edwards et al. | ............... | 514/16 |
| 5,552,520 | A | | 9/1996 | Kim et al. | ................... | 530/311 |
| 5,736,517 | A | | 4/1998 | Bogden et al. | ............... | 514/14 |
| 6,271,202 | B1 | | 8/2001 | Kudsk | ......................... | 514/12 |
| 6,307,017 | B1 | | 10/2001 | Coy et al. | ................... | 530/328 |

OTHER PUBLICATIONS

Minamino et al. Neuromedin C: A bombesin-like peptide identified in porcine spinal cord. Biochemical Biophysical Research Communications, vol. 119, No. 1, pp. 14-20, 1984.*
McDonald et al. Characterization of a gastrin releasing peptide from porcine non antral gastric tissue. Biochemical Biophysical Research Communications, vol. 90, No. 1, pp. 227-233, 1979.*
Phillips-Quagliata et al., 1994 In: Handbook of Mucosal Immunology, pp. 225-239.
Watson and Arkinstall. 1994 In: The G protein-linked receptor facts book, pp. 60-66.
Baraniuk et al., "Bombesin stimulates human nasal mucous and serous cell secretion in vivo", *Lung Cell. Mol. Physiol.* 1992 L48-L-52.
Chu et al., "Bombesin Improves Survival from Methotrexate-Induced Enterocolitis", *Annals of Surgery* 1994 220(4):570-577.
Debas et al., "Neuroendocrine Design of the Gut", *American Journal of Surgery* 1991 161:243-249.
Haskel et al., "Elemental Diet-Induced Bacterial Translocation Can Be Hormonally Modulated", *Annals of Surgery* 1993 217(6):634-643.
Database Prosite Accession No. PDOC00230 Swiss Institute of Bioinformatics; 1989, "Bombesin-like peptides family signature" XP-002348536.
Kawai et al., "Effects of neuromedin B, gastrin-releasing peptide-10 and their fragment peptides on secretion of gastrointestinal and pancreatic hormones in dogs", Acta Endocrinologica (Copenh) 1988 117:205-213.
Kitagawa et al., "Synthesis and Activity of C-Terminal Heptapeptides of Tachykinins and Bombesin-like Peptides[1)]", Chem. Pharm. Bull 1979 27(1):48-57.
Watson et al., "The G-Protein Linked Receptor Factsbook, Passage" London, Academic GB 1994 pp. 60-66 XP009055087.
NCBI Genbank Accession No. AAC59785 [gi:1237140] Mar. 28, 1996 with Revision History, Spindel, E.R.
NCBI Genbank Accession No. AAB19410 [gi:233232] Jan. 21, 1992-May 7, 1993 with Revision History, Conlon, J. M. et al.
NCBI Genbank Accession No. A47201 [gi:422599] Jan. 1, 1900-Sep. 4, 1998 with Revision History, Wechselberger, C. et al.
NCBI Genbank Accession No. P08946 [gi:462543] Nov. 1, 1988-Mar. 1, 2002 with Revision History, Barra, D. et al.
NCBI Genbank Accession No. 0910155A [gi:223763] Jan. 1, 1900-May 2, 1996 with Revision History, Yasuhara. T. et al.
NCBI Genbank Accession No. AAA76076 [gi:997775] Sep. 26, 1995 with Revision History, Spindel, E.R. et al.

* cited by examiner

*Primary Examiner*—Eileen O'Hara
*Assistant Examiner*—Fozia Hamud
(74) *Attorney, Agent, or Firm*—Licata & Tyrrell P.C.

(57) ABSTRACT

The present invention discloses a seven amino acid peptide (7AA) of bombesin. Methods for reducing the impairment respiratory tract mucosal immunity, reducing the rate of infection of the respiratory tract by pathogenic microorganisms and reducing the atrophy or dysfunction of the GALT comprising administering an effective amount of 7AA are also provided.

4 Claims, No Drawings

COMPOSITIONS AND METHODS OF USE FOR A BOMBESIN PEPTIDE

This application is a continuation-in-part of U.S. patent application Ser. No. 09/730,801, filed on Dec. 7, 2000 now U.S. Pat. No. 6,576,611, which is a continuation-in-part of U.S. patent application Ser. No. 08/842,877, filed Apr. 17, 1997 now abandoned, which claim benefit under 35 U.S.C. §119 of U.S. Provisional Application Ser. No. 60/015,835, filed Apr. 19, 1996 and of U.S. Provisional Application Ser. No. 60/029,689, filed Oct. 31, 1996; each of which are incorporated herein by reference.

This invention was made in the course of research sponsored by the National Institutes of Health (NIH Grant No. GM53439). The U.S. government may have certain rights in this invention.

INTRODUCTION

BACKGROUND OF THE INVENTION

Infectious complications are common and critical to patients who are malnourished, sustaining surgical complications, or requiring prolonged intensive care unit (ICU) stays. Despite intravenous (IV) nutrition, multiple antibiotics, and aggressive ICU care, mortality from sepsis (i.e., the presence of pathogenic organisms or their toxins in the blood or tissues) averages 30% with a range of 20–60% depending upon the patient population studied (Bone, et al. (1989) *Cri. Care Med.* 17:389–393; Bone, et al. (1987) *N. Eng. J. Med.* 317:653–658; Ziegler, et al. (1991) *N. Eng. J. Med.* 324:429–436; Hinshaw, et al. (1987) *N. Eng. J. Med.* 317:659–665; and Kreger, et al. (1980) *Am. J. Med.* 68:344–55). Septic morbidity, especially pneumonia, is significantly reduced in these patients when enteral feeding, feeding through a tube into the stomach, is used versus intravenous feeding or no feeding at all is provided (Kudsk, et al. (1996) *Ann. Surg.* 224:531–543; Moore, et al. (1986) *J. Trauma* 26:874–881; Moore, et al. (1989) *J. Trauma* 29:916–923; Moore, et al. (1992) *Ann. Surg.* 216:172–183).

The mechanisms responsible for improved recovery with the use of enteral feeding are poorly understood, but it is hypothesized that lack of enteral feeding leads to a breakdown in the gastrointestinal barrier, allowing molecules and perhaps pathogens to enter the body resulting in inflammation and distant infection (Deitch (1990) *J. Trauma* 30:S184–S189; Deitch (1990) *Surgery* 107:411–416; Ziegler, et al. (1988) *Arch Surg.* 123:1313–1319; Deitch, et al. (1987) *Ann. Surg.* 205:681; Deitch (1988) *Perspect. Crit. Care* 1:1–31. Most investigators have studied barrier integrity by focusing on changes in gut morphology and permeability to bacteria and macromolecules (Bushman, et al. (1993) *Gastroenterology* 104:A612).

Immunoglobulin A (IgA) and secretory IgA (sIgA) are the primary immunological defenses against many mucosal infections to prevent loss of barrier integrity (Svanborg, et al. In: Handbook of Mucosal Immunology (Orga et al., eds.) pp. 71–78; Killian, et al. In: Handbook of Mucosal Immunology (Orga et al., eds.) pp. 127–140). Agents which stimulate sIgA levels in the body include neuropeptides such as bombesin and gastrin-releasing peptide. Intestinal sIgA binds or agglutinates bacteria, viruses, and potentially other toxic molecules which are key to invasive mucosal infection, i.e., IgA prevents adherence of infectious agents to human mucosal cells (Svanborg, et al. In: Handbook of Mucosal Immunology (Orga et al., eds.) pp. 71–78).

Bombesin, a tetradeca-neuropeptide analogous to mammalian gastrin-releasing peptide, is known to stimulate release of a variety of gastrointestinal hormones including gastrin, somatostatin, cholecystokinin, pancreatic polyneuropeptide, insulin, glucagon, and neurotensin (Pascual, et al. In: Handbook of Mucosal Immunology (Orga et al., eds.) pp. 203–216; Debas, et al. (1991) *Am. Surg.* 161:243–249). These hormones then stimulate gastric, pancreatic, and intestinal secretions. In addition, bombesin increases the levels of intestinal sIgA (Debas, et al. (1991) *Am. Surg.* 161:243–249), reduces bacterial translocation (Haskel, et al. (1993) *Ann. Surg.* 217:634–643), and improves mortality in a lethal enterocolitis model (Chu-Ku, et al. (1994) *Ann. Surg.* 220:570–577). Bombesin may also up-regulate specific cellular immunity, either directly or acting through other hormones released in response to its administration (Jin, et al. (1989) *Dig. Dis. Sci.* 34:1708–1712).

In experiments using IV administration of bombesin to stimulate human natural killer (NK) cell activity against human K-562 tumor cells, in vivo bombesin infusion produced a greater antitumor response than in vitro bombesin incubation, suggesting that mediators other than bombesin may be involved in the increased mobilization of active NK cells in the blood stream ((Van Tol, et al. (1993) *J. Neuroimmunol.* 42:139–145). In addition, peripheral blood lymphocytes contain receptors for neurotensin, a neuropeptide released in response to bombesin administration (Evers, et al. (1994) *Surgery* 116:134–140).

Bombesin has been mainly studied for its satiety effect in humans (Gibbs, et al. (1998) *Ann. N.Y. Acad. Sci.* 547:210–216); Hilderbrand, et al. (1991) *Regulatory Neuropeptides* 36:423–433; Muurahainen, et al. (1993) *Am. J. Physiol.* 264: 350–R354; Flynn (1994) *Ann. N.Y. Acad. Sci.* 739:120–134; Lee, et al. (1994) *Neurosci. Biohav. Rev.* 18:313–232). However, binding sites for gastrin-releasing neuropeptide have been documented in human bronchi from specimens obtained from patients undergoing thoracotomy for carcinoma (Baraniuk, et al. (1992) *Neuropeptides* 21:81–84), and bombesin, as well as other neuropeptides, has been found in the respiratory epithelium of the nasal passages (Hauser-Kronberger, et al. (1993) *Acta Otolaryngol.* 113:387–393; Gawin, et al. (1993) *Am. J. Physiol.* 264:L345–350). Moreover, exogenous administration of bombesin stimulates both in vivo and in vitro human nasal mucus and serous cell secretions, thus increasing total protein, lysozyme, and glycoconjugate secretion, and, thereby, acting as a secretagogue in the upper respiratory tract passages (Baraniuk, et al. (1992) *Am. J. Physiol.* 262:L48–L52). No increase in albumin secretion accompanies this increased secretion, suggesting that bombesin does not exert its effects through vasodilation, increases in vascular permeability, or increases in plasma transit across the epithelium.

Investigators who have generated derivatives of bombesin or bombesin-like peptides have focused on amino acid modifications for enhancing antagonist activity. Such modifications include replacement of L-amino acids with D-amino acids; replacement of peptide bonds with non-peptide bonds; replacement of a natural amino acid with a synthetic amino acids such as statine, an AHPPA, or an ACHPA, a β-amino acid, or a γ-amino acid residue; and deletion of the C-terminal amino acid residue (U.S. Pat. No. 6,307,017 to Coy et al.; U.S. Pat. No. 5,428,019 to Edwards et al.; U.S. Pat. No. 5,736,517 to Bogden et al.; U.S. Pat. No. 5,428,018 to Edwards et al.; and U.S. Pat. No. 5,552,520 to Kim et al.).

There remains a need in the art for compositions of bombesin that are small, easy to synthesize, and suitable for pharmaceutical manufacturing and administration.

SUMMARY OF THE INVENTION

One aspect of the present invention provides a composition comprising SEQ ID NO:1. The structure of SEQ ID NO:1 is H-Trp-Ala-Xaa$_1$-Gly-Xaa$_2$-Xaa$_3$-Xaa$_4$-NH$_4$ wherein;
X$_1$ may be Ile, Arg, Thr, or Val;
X$_2$ may be His or Ser;
X$_3$ may be Phe or Leu; and
X$_4$ may be Met, Phe or Leu.

Another aspect of the present invention is directed to methods for reducing the impairment of respiratory tract mucosal immunity comprising administering an effective amount of a composition of SEQ ID NO:1.

Moreover, the present invention is directed to methods of reducing the rate of infection by a pathogenic microorganism in an animal comprising administering an effective of a composition of SEQ ID NO:1.

In addition, the present invention is directed to methods of reducing the atrophy or dysfunction of the small intestinal gut-associated lymphoid tissue (GALT) and generalized mucosal immunity of an animal comprising administering an effective amount of a composition of SEQ ID NO:1.

In a further aspect, effective amounts of a composition of SEQ ID NO:1 may be administered with a pharmaceutically acceptable carrier.

DETAILED DESCRIPTION OF THE INVENTION

Specific cellular and IgA mucosal defense develops after antigen processing and migration of cells to the submucosal spaces (Cebra, et al. In: Handbook of Mucosal Immunology (Ogra et al., eds.) pp. 151–158). Secretory IgA, or sIgA, is a primitive defense used to protect moist epithelial surfaces. sIgA is released at the apical surface of epithelial cells to coat the mucosal surface and bind to bacterial adhesions, preventing attachment to the mucosa and allowing clearance via normal luminal transit. sIgA may also support other cellular responses of immunity. Production and secretion of IgA are controlled by the cytokine milieu created by the T- and B-cell populations of the mucosal lamina propria (Tomasi, TB, In: Handbook of Mucosal Immunology (ogra et al., eds.) pp. 3–8). Therefore, TPN-induced down-regulation of the IgA stimulating cytokines, IL-4 and/or IL-10, may reduce the volume of IgA and cellular responsiveness available for mucosal protection, thereby increasing the risk of bacterial adherence and invasion. Not coincidentally, most nosocomial infections in critically ill ICU patients tend to be due to pathogens which elicit a specific IgA response or are capable of producing an IgA protease, reinforcing that IgA is important for mucosal defense.

The gut-associated lymphoid tissue (GALT) appears to be exquisitely sensitive to route and type of nutrition. Small intestinal GALT is preserved in animals fed Chow or a complex enteral diet, while intravenous TPN produces a generalized atrophy of GALT B and T cells (i.e., B and T lymphocytes) within the lamina propria, Peyer's patches (PP), and intraepithelial spaces. Decreases in intestinal IgA parallel this atrophy. Moreover, the GALT not only provides cells for its own mucosal defense, but it also releases sensitive B and T cells from the PP which home to other mucosal sites, providing significant effector immune function to the respiratory tract, mammary glands, salivary gland, and genitourinary tract (Phillips-Quagliata, et al. In: Handbook of Mucosal Immunology (Ogra et al., eds.) pp. 225–239). IgA produced by these cells plays a role in upper and lower respiratory tract immunity or mucosal defense.

It has now been surprisingly found that a peptide comprising the seven, C-terminal amino acid residues of bombesin (7AA) can, by itself, attenuate TPN-associated depression of intestinal IgA and PP lymphocytes. Though it is known that the biological activities of peptide neurotransmitters reside in the common C-terminus (Watson and Arkinstall (1994) In: The G Protein-Linked Receptor Facts Book, Academic Press. pp 60–66), it was an unexpected finding that the seven amino acid peptide (7AA), by itself, would bind to corresponding receptors and stimulate sIgA production.

In TPN feeding experiments of the instant invention, it was found that 7AA could increase IgA levels to that of animals feed Chow or animals supplemented with bombesin (BBS) during TPN (Table 1).

TABLE 1

| Group | PP Cell No. (×10$^6$/mouse) | Cell No./ PP No. (×10$^4$) | sIgA (µg) |
|---|---|---|---|
| Chow (n = 2) | 7.1 ± 2.5 | 86.0 ± 34.0 | 131.3 ± 5.5 |
| TPN (n = 2) | 1.6 ± 0.4* | 17.3 ± 4.7† | 55.8 ± 8.8†# |
| 7AA-15 (n = 5) | 4.0 ± 0.4† | 35.8 ± 5.0† | 76.4 ± 10.7† |
| 7AA-150 (n = 5) | 3.8 ± 0.3† | 33.5 ± 3.8† | 108.9 ± 5.9 |
| BBS (n = 3) | 3.7 ± 0.7† | 32.3 ± 4.8† | 120.1 ± 21.5 |

*$p < 0.05$ vs Chow, 7AA-15,
†$p < 0.05$ vs Chow.
$p < 0.05$ vs BBS and 7AA-150 (ANOVA).

After a five day feeding regime, sIgA and Peyer's patch (PP) lymphocyte cell numbers were compared in mice fed Chow, TPN, or TPN supplemented with 15 µg/kg body weight BBS (3 injections/day), 15 µg/kg body weight 7AA (7AA-15; 6 injections over a 10 hour period/day), or 150 µg/kg body weight 7AA (7AA-150; 6 injections over a 10 hour period/day). Lymphocyte cell numbers per PP for animals injected with either 7AA-15 or 7AA-150 exceeded those of animals injected with BBS. Moreover, there was a dose-dependent effect of 7AA on sIgA levels. 7AA administered at 150 µg/kg body weight was nearly 1.5 times more effective than 7AA administered at 15 µg/kg body weight at increasing sIgA levels.

Further investigations were conducted to evaluate an effective dose of 7AA; higher concentrations of 7AA were administered with fewer injections per day. 7AA was administered at 15 µg/kg/injection, 6 times per day (7AA-15-6); 150 µg/kg/injection, 3, 5, and 6 times per day (7AA-150-3, 7AA-150-5, and 7AA-150-6, respectively); and 3 injections per day of 450, 1350, and 2700 µg/kg/injection (7AA-450-3, 7AA-1350-3, and 7AA-2700-3, respectively). After a five day feeding regime PP lymphocyte cell numbers were compared amongst mice fed Chow, TPN, or TPN supplemented with 15 µg/kg body weight BBS (3 injections/day) or the various 7AA amounts outlined above.

TABLE 2

| Group | PP Cell No. (10$^6$/mouse) | PP No. | Cell No./PP No. (×10$^4$) |
|---|---|---|---|
| Chow (n = 6) | 6.8 ± 1.0 | 13.0 ± 3.0 | 67.1 ± 13.9 |
| TPN (n = 7) | 1.9 ± 0.3† | 10.3 ± 0.9 | 16.9 ± 2.3† |

TABLE 2-continued

| Group | PP Cell No. (10⁶/mouse) | PP No. | Cell No./PP No. (×10⁴) |
|---|---|---|---|
| BBS (n = 7) | 3.8 ± 0.7*† | 13.5 ± 0.5 | 30.5 ± 4.8† |
| 7AA-15-6 (n = 5) | 4.0 ± 0.4*† | 11.2 ± 0.4 | 35.8 ± 5.1*† |
| 7AA-150-3 (n = 3) | 5.8 ± 1.2* | 14.3 ± 0.9 | 39.9 ± 6.5*† |
| 7AA-150-5 (n = 4) | 5.4 ± 0.8* | 10.8 ± 1.4 | 49.8 ± 1.7* |
| 7AA-150-6 (n = 5) | 3.8 ± 0.3*† | 11.6 ± 0.7 | 33.5 ± 3.8† |
| 7AA-450-3 (n = 4) | 4.4 ± 0.7*† | 12.3 ± 0.9 | 35.1 ± 4.1† |
| 7AA-1350-3 (n = 3) | 5.0 ± 0.9* | 11.0 ± 0.6 | 51.8 ± 5.8* |
| 7AA-2700-3 (n = 2) | 4.8 ± 0.4* | 14.0 ± 0.0 | 34.6 ± 2.9† |

Data are presented as means ± SEM.
*$p < 0.05$ vs TPN,
†$< 0.05$ vs Chow.

Table 2 summarizes the results of this study. As in the previous experiment, 7AA-treated mice had more lymphocytes cells per PP than did than those treated with BBS. The optimal regimes were injection of 150 µg/kg 7AA, 5 times per day, or 1350 µg/kg 7AA, 3 times per day.

Results of experiments comparing 7AA and bombesin (BBS) show that 7AA is as effective or more effective than BBS in improving mucosal immunity defects induced by intravenous feeding in animals. Therefore, it is to be understood that methods involving administering BBS may also be carried out with a composition of 7AA. The advantage of using 7AA over BBS is better dosage efficiencies and ease of synthetic synthesis of short peptides.

Since intestinal and extra-intestinal immunity are closely linked via the common mucosal immune system, and neuropeptides, such as bombesin, and bombesin-like neuropeptides, attenuate TPN-induced GALT atrophy, exogenous administration of such neuropeptides reverses, and preferably prevents, the impairment of respiratory tract mucosal immunity known to occur following IV-TPN in immunized animals to an IgA-mediated infectious viral challenge or to bacteria known to generate a specific IgA response. The present invention provides a composition of 7AA used to prevent mucosal immunity impairment and depressed intestinal IgA levels. Bombesin and 7AA have broader effects, including up-regulation of extra-intestinal mucosal immunity.

The present invention provides a composition comprising SEQ ID NO:1. The structure of SEQ ID NO:1 is H-Trp-Ala-Xaa$_1$-Gly-Xaa$_2$-Xaa$_3$-Xaa$_4$-NH$_4$ wherein;

$X_1$ may be Ile, Arg, Thr, or Val;

$X_2$ may be His or Ser;

$X_3$ may be Phe or Leu; and $X_4$ may be Met, Phe or Leu.

Amino acids comprising the structure of SEQ ID NO:1 may be naturally occurring amino acids of wholly or partially synthetic derivatives.

The composition of the present invention may also comprise one or more pharmaceutically acceptable carriers, other adjuvants, and active substances. Exemplary pharmaceutical carriers and adjuvants are described in U.S. Pat. No. 5,397,803, which is specifically incorporated by reference.

The invention is directed to methods for reducing, preferably eliminating, impairment of respiratory tract mucosal immunity and, in particular, upper and lower respiratory tract mucosal immunity, associated with a lack of enteral feeding of complex diet(s) (e.g. Chow or complex enteral diet (CED)) or lack of immunological stimulation of the gastrointestinal (GI) tract in animals. Methods according to this embodiment of the invention entail administering to an animal an effective amount of a composition of SEQ ID NO:1.

Another embodiment of the present invention is directed to methods of reducing the rate of infection, preferably preventing infection, of the respiratory tract and, in particular, the upper and lower respiratory tract, caused by pathogenic microorganisms such as viruses, bacteria, fungi, etc., associated with a lack of enteral feeding of complex diet(s) (e.g. Chow or CED) or a lack of immunological stimulation of the GI tract in animals. Risk of infection, such as pneumonia, occurring in the upper and lower respiratory tract may also be reduced or, preferably, prevented by such methods. Methods according to this embodiment of the invention entail administering to an animal an effective amount of a composition of SEQ ID NO:1.

The invention is further directed to methods for reducing the atrophy or dysfunction of the small intestinal gut-associated lymphoid tissue (GALT) of an animal associated with a lack of enteral feeding of complex diet(s) (e.g. Chow, CED, or other foods) or a lack of immunological stimulation of the GI tract. The methods entails administering to the animal an effective amount of a composition of SEQ ID NO:1.

For both the methods and compositions of the invention, an effective amount is defined as an amount which reduces or prevents the impairment of GI and/or upper and lower respiratory tract mucosal immunity. According to the present invention, an effective amount of SEQ ID NO:1 may preferably vary from about 150 µg/kg to about 2 mg/kg, with administration rates of about 3 to about 4 times per day. Preferably, the amount of a composition of SEQ ID NO:1 administered daily may range from about 0.1 g/kg body weight to about 5.0 g/kg body weight.

Preferably, a composition of SEQ ID NO:1 is administered as a supplement to a patient's TPN if TPN is used. Examples of parenteral routes of administration include, but are not limited to, subcutaneous, intramuscular, respiratory, or IV injection, as well as nasopharyngeal, mucosal, and transdermal absorption. A composition of SEQ ID NO:1 can also be administered via the gastrointestinal tract in a protected form, such as where the protected form is a liposome.

EXAMPLES

Example 1

Animal Care

The studies prepared herein conform to the guidelines for the care and use of laboratory animals established by the Animal Care and Use Committee of The University of Tennessee, and protocols were approved by that committee. Male ICR mice (Harlan, Indianapolis, Ind.) were housed in an American Association for Accreditation of Laboratory Animal Care accredited conventional facility under controlled conditions of temperature and humidity with a 12:12 hour light: dark cycle. Mice were quarantined and fed commercial mouse Chow (RMH 3200 Agway, Syracuse, N.Y.) with water ad libitum for 2 weeks prior to protocol entry. During the experiments, the mice were housed in metal metabolism cages with wire-grid bottoms to eliminate coprophagis and bedding ingestion.

Example 2

Experimental Protocol

Mice underwent placement of catheters for IV infusion after intraperitoneal injection of Ketamine (100 mg/kg body weight) and Acepromazine Maleate (10 mg/kg body weight) mixture. A silicone rubber catheter (0.012 inch I.D.×0.025% O.D., Baxter, Chicago, Ill.) was inserted into the vena cava through the right jugular vein. The distal end of the catheter was tunneled subcutaneously and exited the tail at its midpoint. Animals were partially immobilized by tail restraint during infusion; this model does not produce physical or chemical evidence of stress (Sitren, et al. (1983) *JPEN* 7:582–586).

Catheterized animals were immediately infused with saline at a rate of 4 ml per day. For the first two days, animals were allowed ad libitum access to Chow and then randomized to various experimental diets. The Chow group (Chow) served as the control group and received an infusion of physiologic saline in addition to standard laboratory mouse diet and water ad libitum. The total parenteral nutrition (TPN) group received a stand TPN solution intravenously (Li, et al. (1995) *J. Trauma* 39:44–52). The TPN solution contains 4.1% amino acids and 34.3% glucose (1538 kcal/L), in addition to electrolytes and vitamins. The non-protein calorie/nitrogen ratio of the TPN solution was 158:1 kcal/g nitrogen. The bombesin group (BBS) received an identical TPN solution, as well as bombesin, given by slow IV infusion through their venous catheters, every eight hours at a dose of 15 µg/kg body weight. The seven amino acid bombesin peptide group (7AA) received 7AA in the same manner that BBS was administered. The groups receiving 7AA were injected a variable amount of 7AA at various times per day. During the postoperative Chow feeding, the infusion rates of saline via the respective catheters were increased over a 48-hour period to 10 ml/day and were continued at those rates for the five days of experimental diet feeding. This feeding regime provided ~15 kcal energy and 95 mg nitrogen, meeting the calculated requirements for mice weighing 25 to 30 g (Nutrient Requirements of Laboratory Animals. National Research Council Publication No. 10, National Academy of Science, 1978).

After five days of their respective diets, animals were sacrificed by exsanguination under anesthesia. The small intestine was excised from the ligament of Treitz to the ileocecal valve and rinsed three times with a total of 15 ml chilled Hanks' balanced salt solution (HBSS), and the intestinal contents collected in plastic tubes in an ice bath. The length of the small intestine segments was recorded under a standardized vertical extension with a 2-gram weight and the contents stored in −70° C. freezer for further IgA analysis.

Example 3

Antibody Quantitation

IgA was measured in intestinal washings in a sandwich enzyme-linked immunosorbent assay (ELISA), using a polyclonal goat anti-mouse IgA (Sigma, St. Louis, Mo.) to coat the plate, a purified mouse IgA (Sigma, St. Louis, Mo.) as standard, and a horseradish peroxidase-conjugated goat anti-mouse IgA.

Example 4

Cell Isolations

Lymphocyte isolations from the Peyer's patches (PP) were performed as previously described (Li, et al. (1995) *J. Trauma* 39:44–52). The PP were excised from the serosal side of the intestine and teased apart with 18-guage needles. The fragments were treated with Type 1 collagenase (Sigma, St. Louis, Mo.) (50 U/ml) in minimal essential medium (MEM) for 60 minutes at 37° C. with constant rocking. After collagenase digestion, the cell suspensions were passed through nylon fibers. The number of lymphocytes in PP were counted by hemocytometer.

---

What is claimed is:

1. A composition comprising an isolated peptide consisting of H-Trp-Ala-Xaa$_1$-Gly-Xaa$_2$-Xaa$_3$-Xaa$_4$-NH$_4$ (SEQ ID NO:1) and a pharmaceutically acceptable carrier, wherein Xaa$_1$ is Ile, Arg, Thr or Val;

Xaa$_2$ is His or Ser;

Xaa$_3$ is Phe or Leu; and

Xaa$_4$ is Met, Phe or Leu.

2. A method of reducing impairment of respiratory tract mucosal immunity in an animal associated with a lack of enteral feeding or a lack of immunological stimulation of the gastrointestinal tract, comprising administering an effective amount of the composition of claim 1.

3. A method of reducing the rate of infection of the respiratory tract by a pathogenic microorganism in an animal associated with a lack of enteral feeding or a lack of immunological stimulation of the gastrointestinal tract comprising administering an effective amount of the composition of claim 1.

4. A method of reducing the atrophy or dysfunction of the GALT of an animal associated with a lack of enteral feeding or a lack of immunological stimulation of the gastrointestinal tract comprising administering to the animal an effective amount of the composition of claim 1.

* * * * *

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: 7AA Synthetic Peptide.
<220> FEATURE:
<221> NAME/KEY: MISC_FEATURE
<222> LOCATION: (3)..(3)
<223> OTHER INFORMATION: X may be Ile, Arg, Thr, or Val.
<220> FEATURE:
<221> NAME/KEY: MISC_FEATURE
<222> LOCATION: (5)..(5)
<223> OTHER INFORMATION: X may be His or Ser.
<220> FEATURE:
<221> NAME/KEY: MISC_FEATURE
<222> LOCATION: (6)..(6)
<223> OTHER INFORMATION: X may be Phe or Leu.
<220> FEATURE:
<221> NAME/KEY: MISC_FEATURE
<222> LOCATION: (7)..(7)
<223> OTHER INFORMATION: X may be Met, Phe or Leu.

<400> SEQUENCE: 1
```

```
-continued

Trp Ala Xaa Gly Xaa Xaa Xaa
1               5

1
```